United States Patent [19]

Blessing et al.

[11] Patent Number: 5,110,990

[45] Date of Patent: May 5, 1992

[54] PROCESS FOR RECOVERY OF PHOSPHORUS LIGAND FROM VAPORIZED ALDEHYDE

[75] Inventors: Michael A. Blessing, Sissonville, W. Va.; Gregory J. Dembowski, League City, Tex.; Gregory K. Finnell, Charleston, W. Va.

[73] Assignee: Union Carbide Chemicals & Plastics Technology Corporation, Danbury, Conn.

[21] Appl. No.: 370,126

[22] Filed: Jun. 22, 1989

Related U.S. Application Data

[63] Continuation of Ser. No. 595,408, Mar. 30, 1984, abandoned.

[51] Int. Cl.$^5$ .............................................. C07C 45/00
[52] U.S. Cl. ..................................... 568/492; 568/454
[58] Field of Search ............................... 568/454, 492

[56] References Cited

U.S. PATENT DOCUMENTS

| | | | |
|---|---|---|---|
| 3,539,634 | 11/1970 | Olivier et al. | 260/604 |
| 4,166,773 | 9/1979 | Higley et al. | 203/72 |
| 4,242,284 | 12/1980 | Harris et al. | 568/454 |
| 4,247,486 | 1/1981 | Brewster et al. | 568/454 |
| 4,283,562 | 8/1981 | Billig et al. | 568/454 |
| 4,298,541 | 11/1981 | Oswald et al. | 260/429 R |
| 4,390,729 | 1/1983 | Oswald | 568/454 |
| 4,400,548 | 8/1983 | Abatjoglou et al. | 568/454 |
| 4,482,749 | 11/1984 | Dennis et al. | 568/454 |

FOREIGN PATENT DOCUMENTS

| | | |
|---|---|---|
| 0016285 | 10/1980 | European Pat. Off. . |
| 0016286 | 10/1980 | European Pat. Off. . |
| 0096986 | 12/1983 | European Pat. Off. . |
| 0096987 | 12/1983 | European Pat. Off. . |
| 0096988 | 12/1983 | European Pat. Off. . |
| WO80/01690 | 8/1980 | PCT Int'l Appl. . |

*Primary Examiner*—Bruce Gray
*Attorney, Agent, or Firm*—Reynold J. Finnegan

[57] ABSTRACT

An improved rhodium catalyzed liquid recycle hydroformylation process, the improvement which comprises selectively separating and recovering phosphorus ligand from the vaporized aldehyde product stream obtained from volatilizing and separating the aldehyde product from the catalyst containing reaction product solution of the hydroformylation process.

13 Claims, No Drawings

PROCESS FOR RECOVERY OF PHOSPHORUS LIGAND FROM VAPORIZED ALDEHYDE

This application is a continuation of prior U.S. application Ser. No. 595,408 filed Mar. 30, 1984 now abandoned.

FIELD OF THE INVENTION

This invention relates to an improved rhodium catalyzed liquid recycle hydroformylation process, the improvement which comprises selectively separating and recovering phosphorous ligand from the vaporized aldehyde product stream obtained after volatilizing and separating the aldehyde product from the catalyst containing reaction product solution of the hydroformylation process.

BACKGROUND OF THE INVENTION

Methods for producing aldehydes by the hydroformylation of an olefinically unsaturated organic compound with carbon monoxide and hydrogen in the presence of a rhodium-phosphorus complex catalyst and free phosphorus ligand are well known in the art as seen e.g. by the basic low pressure oxo hydroformylation process of U.S. Pat. No. 3,527,809 and the rhodium catalyzed liquid recycle hydroformylation process of U.S. Pat. No. 4,148,830.

For instance, U.S. Pat. No. 3,527,809 discloses a basic hydroformylation process wherein olefinically unsaturated organic compounds are hydroformylated with carbon monoxide and hydrogen in the presence of a rhodium-phosphorus complex catalyst and free phosphorus ligand to produce aldehydes in high yields at low temperatures and low pressures.

It is also known that under such hydroformylation conditions, some of the product aldehydes condense to form higher boiling aldehyde condensation by-products, such as dimers, trimers and the tetramers. U.S. Pat. No. 4,148,830 discloses the use of these higher boiling liquid aldehyde condensation by-products as a reaction solvent for the catalyst which also makes an excellent carrier for a continuous liquid recycle process. For example, such continuous liquid recycle processes, involve removal from the reactor of some of the liquid reaction aldehyde product solution containing aldehyde product, the solubilized rhodium-phosphorus complex catalyst, free phosphorus ligand and the higher boiling aldehyde condensation by-products, and separating the aldehyde product therefrom by rapidly volatilizing the aldehyde product. The volatilized aldehyde product and non-volatilized catalyst containing liquid reaction solution is then disengaged in a gas-liquid separator, wherein the vaporized aldehyde product vapor stream is passed overhead for recovery and the remaining condensed non-volatilized catalyst containing liquid reaction solution removed from the bottom and recycled back to the reactor.

However, a disadvantage found attendant with liquid catalyst recycle hydroformylation processes is the loss of phosphorus ligand during the process due to containment of volatilized phosphorus ligand in the vaporized aldehyde product stream obtained upon the volatilized separation of the aldehyde product from the liquid catalyst containing reaction product solution. In commercial scale operations such ligand loss can not only represents a stiff economic penalty due to the physical loss of the ligand, but renders further processing of the crude aldehyde product necessary if damage to downstream aldehyde hydrogenation system catalysts employed in producing alcohols from the aldehyde is to be prevented or at least minimized. For instance, a primary known use of such aldehydes is to produce alcohols via hydrogenation and phosphorus ligand contained in the crude aldehyde product has been found to cause deactivation of such hydrogenation catalysts.

Attempts to purify the crude aldehyde product by passing the volatilized aldehyde product through sophisticated entrainment equipment such as packed columns or trays is not considered a satisfactory answer to the problem. While such sophisticated methods may be suitable for removing and recovering entrained liquids in the vaporized aldehyde product steam they may also promote the formation of more higher boiling aldehyde condensation by-products. Likewise purification of the crude aldehyde product by condensation and redistillation only serves to also further promote aldehyde product loss by the formation of more higher boiling aldehyde condensation by-products, which disadvantage is further compounded by the direct loss of even more aldehyde that remains with the condensation by-products during such a separation procedure.

Thus there remains a need in liquid catalyst recycle hydroformylation for a simple and effective method for selectively removing and recovering the vaporized phosphorus ligand contained in the vaporized aldehyde product stream obtained during a continuous liquid recycle rhodium catalyzed hydroformylation process.

SUMMARY OF THE INVENTION

It has now been discovered that vaporized phosphorus ligand can be selectively separated and recovered from a vaporized aldehyde product stream containing said ligand and obtained during a continuous liquid rhodium catalyst recycle hydroformylation process by contacting said aldehyde product stream with a dispersed liquid so as to selectively condense the vaporized phosphorus ligand from said aldehyde product stream, which condensed phosphorus ligand may then be recovered and employed as desired.

More specifically this invention can be described as an improved liquid recycle rhodium catalyzed hydroformylation process for producing aldehydes, wherein an olefinic compound, carbon monoxide and hydrogen are reacted in the presence of a solubilized rhodium-phosphorus complex catalyst, free phosphorus ligand and higher boiling aldehyde condensation by-products to produce an aldehyde product and wherein said aldehyde is separated and recovered from a liquid reaction aldehyde product solution containing aldehyde product, solubilized rhodium-phosphorus complex catalyst, free phosphorus ligand and higher boiling aldehyde condensation by-products that has been removed from the hydroformylation reactor, by vaporizing the aldehyde product contained in said solution to obtain a vaporized aldehyde product stream consisting essentially of vaporized aldehyde product, vaporized phosphorus ligand and vaporized higher boiling aldehyde condensation by-products which is disengaged in a separator from the remaining non-volatilized catalyst containing liquid reaction product solution that is recovered from the bottom of the separator and recycled back to the reaction system, the improvement comprising (a) selectively separating the phosphorus ligand and vaporized higher boiling aldehyde condensation by-products contained in said vaporized aldehyde product stream by thoroughly contacting said stream with a dispersed liquid having a lower boiling point than said higher boiling aldehyde condensation by-products so as to condense vaporized phosphorus ligand and vaporized higher boiling aldehyde condensation by-products contained in said volatilized aldehyde product stream, and (b) recovering the condensed phosphorus ligand and condensed higher boiling aldehyde condensation by-products so obtained from the volatilized aldehyde product stream, said dispersed liquid being employed in the form of droplets and in an amount such that the percent of phosphorus ligand so separated and recovered is at least about 1.2 times higher than the percent of higher boiling aldehyde by-products also so separated and recovered.

DETAILED DESCRIPTION

This invention is applicable to improving any conventional continuous liquid recycle rhodium-phosphorus complex catalyzed hydroformylation process for producing aldehydes, which process is conducted in the presence of free organic phosphorus ligand. Such oxo processes and the conditions thereof are well known in the art as illustrated, e.g. by the continuous liquid recycle process of U.S. Pat. No. 4,148,830. Such hydroformylation processes in general involve producing aldehydes by reacting an olefinic compound with hydrogen and carbon monoxide gas in a liquid reaction medium which contains a soluble rhodium phosphorus complex catalyst, free organophosphorus ligand and higher boiling aldehyde condensation by-products and wherein the hydroformylation reaction conditions may comprise a temperature of from about 50° C. to 200° C. and a total gas pressure of hydrogen, carbon monoxide and olefinic compound of from about 1 to 10,000 psia.

Of course it is to be understood that the particular manner in which the hydroformylation reaction is carried out and particular hydroformylation reaction conditions employed are not critical to the subject invention and may be varied widely and tailored to meet individual needs and produce the particular aldehyde product desired.

Accordingly the olefinic starting material reactants encompassed by the process of this invention can be terminally or internally unsaturated and be of straight-chain, branched-chain or cyclic structure. Such olefins can contain from 2 to 20 carbon atoms and may contain one or more ethylenic unsaturated groups. Moreover, such olefins may contain groups or substituents which do not essentially adversely interfere with the hydroformylation process such as carbonyl, carbonyloxy, oxy, hydroxy, oxycarbonyl, halogen, alkoxy, aryl, haloalkyl, and the like. Illustrative olefinic unsaturated compounds include alpha olefins, internal olefins, alkyl alkenoates, alkenyl alkanoates, alkenyl alkyl ethers, alkenols, and the like, e.g. ethylene, propylene, 1-butene, 1-pentene, 1-hexene, 1-octene, 1-decene, 1-dodecene, 1-octadecene, 2-butene, 2-methyl propene (isobutylene), isoamylene, 2-pentene, 2-hexene, 3-hexene, 2-heptene, cyclohexene, propylene dimers, propylene trimers, propylene tetramers, 2-ethyl-1-hexene, styrene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl-7-octenoate, 3-butenenitrile, 5-hexenamide, and the like.

Of course, it is understood that mixtures of different olefinic starting materials can be employed, if desired, by the hydroformylation process of the subject invention. Among the more preferred olefins are alpha olefins containing from 2 to 8 carbon atoms and internal olefins containing from 4 to 8 carbon atoms as well as starting material mixtures of such alpha olefins and internal olefins. The most preferred olefin starting materials are ethylene, propylene, butene-1, butene-2 (cis and/or trans), isobutene and various mixture thereof.

Likewise any conventional rhodium-phosphorus complex catalyst can be employed and such catalysts as well as methods for their preparation are well known in the art. Such rhodium-phosphorus complex catalysts may include any of the rhodium-organophosphine or rhodium-organophosphite complex hydroformylation catalyst heretofore advanced for such hydroformylation processes. Of course mixtures of such catalysts can also be employed if desired. Moreover, it is clear that the amount of complex catalyst present in the reaction medium of a given process need only be that minimum amount necessary to provide the rhodium metal concentration desired to be employed and which will furnish the basis for at least that catalytic amount of rhodium metal necessary to catalyze the particular hydroformylation process desired. In general, rhodium metal concentrations in the range of from about 10 ppm to about 1000 ppm, calculated as free metal, should be sufficient for most hydroformylation processes. It is generally preferred to employ from about 10 to 500 ppm of rhodium and more preferably from 25 to 350 ppm of rhodium, calculated as free metal.

As noted above, the hydroformylation process of this invention is carried out in the presence of free phosphorus ligand, i.e. ligand that is not complexed with the rhodium complex catalyst employed. However, while it is generally preferred that the free phosphorus ligand be the same as the phosphorus ligand of the rhodium-phosphorus complex catalyst such is not necessary and different ligands can be employed in a given process, if desired. Accordingly as in the case of the complex catalyst any conventional organophosphorus ligand can be employed as the free ligand and such ligands as well as methods for their prparation are well known in the art. Such free phosphorus ligands may include any of the organophosphine or organophosphite ligands heretofore advanced for such hydroformylation processes. Of course mixtures of such ligands can also be employed if desired. Thus the hydroformylation process of this invention may be carried out in any excess amount of free phosphorus ligand, e.g. at least one mole of free phosphorus ligand per mole of rhodium metal present in the reaction medium. The amount of free phosphorus ligand employed in general merely depends upon the aldehyde product desired, and the olefin and complex catalyst employed. Accordingly amounts of free phosphorus ligand present in the reaction medium ranging from about 1 to about 300 or more per mole of rhodium present should be suitable for most purposes. For example in general large amounts of free triarylphosphine ligand, e.g. triphenylphosphine, such as more than 50 or more preferably more than 100 moles of free ligand per mole of rhodium have preferably been employed to achieve satisfactory catalytic activity and/or catalyst stabilization, while other phosphorus ligands, e.g. alkylarylphosphines and cycloalkylarylphosphines may help provide acceptable catalyst stability and reactivity without unduly retarding the conversion rates of certain olefins to aldehydes when the amount of free ligand present in the reaction medium is as little as 1 to 100 and more preferably 15 to 60 moles per mole of rhodium present.

More particularly illustrative rhodium-phosphorus complex catalysts and illustrative free phosphorus ligands include, e.g. those disclosed in U.S. Pat. Nos. 3,527,809; 4,148,830; 4,283,562; 4,400,548, European Patent Applications, Publication Nos. 96,986; 96,987 and 96,988 (all published Dec. 28, 1983); PCT patent application, Publication No. WO 80/01690 (published Aug. 21, 1980) and U.S. application Ser. No. 581,352 filed Feb. 17, 1984 now U.S. Pat No. 4,599,206. Among the more preferred ligands and complex catalysts that may be mentioned are, e.g. the triphenylphosphine ligand and rhodium-triphenylphosphine complex catalysts of U.S. Pat. No. 3,527,809 and 4,148,830; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the diorganophosphite ligands and rhodium-diorganophosphite complex catalysts of U.S. application Ser. No. 581,352 filed Feb. 17, 1984.

As further noted above the hydroformylation reaction is carried out in the presence of higher boiling aldehyde condensation by-products. It is the nature of such continuous hydroformylation reactions employable herein to produce such higher boiling aldehyde by-products (e.g. dimers, trimers and tetramers) in situ during the hydroformylation process as explained more fully, e.g. in U.S. Pat. Nos. 4,148,830 and 4,247,486. Such aldehyde by-products provide an excellent carrier for the liquid catalyst recycle process. Indeed, while one may employ, if desired, any suitable solvent at the start up of a continuous process (aldehyde compounds corresponding to the desired aldehyde products being preferred), the primary solvent will normally eventually comprise both aldehyde products and higher boiling aldehyde condensation by-products due to the nature of such continuous processes. Of course aldehyde condensation by-products can also be preformed if desired and used accordingly. Of course it is also obvious that the amount of such higher boiling aldehyde by-products present in the reaction medium may vary over wide limits and is generally governed only by equipment constraints and the particular aldehyde product to be produced. For example, initially the hydroformylation reaction can be effected in the absence or in the presence of small amounts of higher boiling aldehyde condensation by-products as a solvent for the rhodium complex catalyst, or the reaction can be conducted with upwards to 70 weight percent, or even as much as 90 weight percent, and more of such condensation by-products, based on the total liquid medium. In general ratios of aldehyde to higher boiling aldehyde condensation by-products within the range of from about 1:4 to about 4 to 1 by weight should be sufficient for most purposes. Likewise it is to be understood that minor amounts of other conventional organic cosolvents may be present if desired.

While the hydroformylation reaction conditions may vary over wide limits as discussed above in general it is more preferred that the process be operated at a total gas pressure of hydrogen, carbon monoxide and olefinic unsaturated starting compound of less than about 1500 psia and more preferably less than about 500 psia. The minimum total pressure of the reactants is not particularly critical and is limited predominately only by the amount of reactants necessary to obtain a desired rate of reaction. More specifically the carbon monoxide partial pressure of the hydroformylation process of this invention is preferably from about 1 to about 120 psia and more preferably from about 3 to about 90 psia, while the hydrogen partial pressure is preferably about 15 to about 160 psia and more preferably from about 30 to about 100 psia. In general $H_2$:CO molar ratio of gaseous hydrogen to carbon monoxide may range from about 1:10 to 100:1 or higher, the more preferred hydrogen to carbon monoxide molar ratio being from about 1:1 to about 10:1.

Further as noted above the hydroformylation process of this invention may be conducted at a reaction temperature from about 50° C. to about 200° C. However in general, hydroformylations at reaction temperatures of about 70° C. to about 120° C. and more preferably about 90° C. to about 110° C. are preferred for most types of olefinic starting materials.

As outlined herein the hydroformylation process of this invention involves a continuous liquid catalyst recycle system wherein a portion of the liquid reaction aldehyde product solution containing aldehyde product, solubilized rhodium-phosphorus complex catalyst, free phosphorus ligand and higher boiling aldehyde condensation by-products is removed from the reactor and wherein the desired aldehyde product is separated via vaporization or distillation, in one or more stages, under normal, reduced or elevated pressure from the liquid reaction solution, condensed and collected in a product receiver, and further purified if desired, and the remaining non-volatilized catalyst containing liquid reaction product solution is recycled back to the reactor. Such types of continuous hydroformylation systems and methods for carrying them out are well known in the art and thus need not be particularly detailed herein. In general the volatilized aldehyde product is disengaged from the liquid in any suitable gas-liquid separator wherein the volatilized aldehyde product stream is passed overhead and the remaining non-volatilized liquid catalysts containing reaction product solution is collected from the bottom of the separator and recycled back to the reaction system. Volatilization of the aldehyde product can be conducted in any conventional manner. Preferably an evaporator or vaporizer is employed which will effect a residence time which is short enough to avoid or minimize the degree of possible decomposition of the heat sensitive rhodium-phosphorus complex catalyst present in the reaction product stream. For instance such allows the aldehyde product to be volatilized at high temperatures in a matter of minutes or more preferably seconds thus minimizing any harm to the heat sensitive catalyst. In general volatilization temperatures may be as high as 150° C. or more, although it is generally preferred to employ temperatures below 150° C. when possible. Illustrative suitable vaporizers include a falling film evaporator, a thin film evaporator, a wiped film evaporator, a scraped surface type evaporator and the like, with preference given in practice to the use of a falling film evaporator. While the vaporized aldehyde product can be disengaged from the remaining non-volatilized liquid catalyst containing reaction product solution in sophisticated and costly gas-liquid separators in commercial practice it is generally preferred to employ a simple non-intricate catchpot separator wherein the aldehyde product vapor stream is passed overhead for eventual recovery of the desired aldehyde product. It has been further commonplace to pass the aldehyde product vapor stream through an entrainment device having a demisting pad for return to the separator of any liquid that may be entrained in the vapor stream so removed. The remaining non-volatilized liquid catalyst containing reaction product solution is then simply recovered from the bottom of the separator and recycled back to the reactor system, after passing the liquid recycle through a cooler such as a falling film cooler, if desired, and/or after any other purification or catalyst regeneration procedure, if desired. Moreover it is to be understood that, if desired the hydroformylation process of this invention can also involve, if desired, any other conventional processing procedures that do not have any unduly adverse effect on the point of novelty of this invention such as, e.g. flash distillation of lites, e.g. unreacted olefin, alkanes, carbon monoxide, hydrogen, and the like from the liquid reaction product solution prior to vaporization of the desired aldehyde product.

It has now been discovered that such above discussed continuous liquid catalyst recycle hydroformylation processes may be improved by selectivity separating and recovering phosphorus ligand contained in the vaporized aldehyde product steam of such processes, that might otherwise be lost due to volatilization along with the vaporized aldehyde product. Moreover, the improvement procedure of this invention may be carried out by thoroughly contacting the vaporized aldehyde product stream with a dispersed liquid having a lower boiling point then the higher boiling aldehyde condensation by-products also contained in said stream so as to condense the vaporized phosphorus ligand contained in said aldehyde product steam into liquid phosphorus ligand droplets and recovering said condensed liquid phosphorus ligand from the aldehyde product vapor stream.

As noted above the vaporised aldehyde product stream separated from the liquid catalyst containing aldehyde product solution removed from the reactor consists essentially of vaporized aldehyde product, vaporized phosphorus ligand and vaporized higher boiling aldehyde condensation by-products, the concentration of ligands and by-products contained in said vaporized product stream being mainly dependent upon the amount of ligand and by-product present in the liquid product from which said vaporized product stream is disengaged. Of course, it is understood that said vaporized aldehyde product stream may also contain minor amounts of vaporized lites as well such as unreacted olefin, alkanes, carbon monoxide, hydrogen and the like, which are immaterial to the subject invention.

Applicants have discovered that by thoroughly contacting the vaporized aldehyde product stream with a suitable dispersed liquid, that the vaporized phosphorus ligand contained therein will not only be condensed into recoverable liquid droplets, but also that by controlling the amount of dispersed liquid employed that the percent of phosphorus ligand so separated can be selectively appreciably higher than the percent of higher boiling aldehyde by-products also so condensed and separated from said volatilized aldehyde product stream. Thus the subject improvement of this invention is unique in that it allows for selective separation and recovery of the phosphorus ligand contained in the vaporized aldehyde product stream while minimizing the amount of higher boiling aldehyde by-products that is also so separated and recovered by the same procedure.

While not intending to be bound by any precise theory, by way of an explanation, the condensation of the vaporized phosphorus ligand contained in the vaporized aldehyde product stream is caused by the vaporized aldehyde product stream which is at about its dewpoint coming into contact with the dispersed liquid droplets, thereby volatilizing or at least partially volatilizing the dispersed liquid droplets almost instantly so as to cool the aldehyde product vapor stream below its dewpoint and thereby cause the heavier components of said vapor stream which are the phosphorus ligand and higher boiling aldehyde condensation by-products to condense into droplets of said ligand and said by-products which can readily be recovered in any appropriate manner. In addition, it is also considered that this subject procedure of condensation of volatilized ligand and by-products may also cause any initially entrained liquid phosphorus ligand and/or higher boiling aldehyde condensation by-products in said aldehyde product vapor stream to agglomerate into larger and more easily separable drops of liquid.

Accordingly, the dispersed liquid employed in this invention can be any suitable liquid which will be vaporized or at least partially vaporized at the dewpoint of the vaporized aldehyde product stream when it is thoroughly contacted (mixed) therewith. Of course, it is understood that the dispersed liquid should be compatible with both the product aldehyde and the catalyst solution from which the aldehyde vapor stream has been disengaged, so that it will not cause any undue adverse effect to the aldehyde product and the catalysts solution if said ligand and by-products so recovered are to be returned to the reactor system. Likewise, the preferred liquid should be of purity that it does not foul the dispersing device employed or separator employed in recovering the desired phosphorus ligand. It is further preferred that the dispersed liquid have sufficient volatility at the dewpoint of the vaporized aldehyde product stream with which it is contacted so that if returned to the reactor system, it does not accumulate in the catalyst solution to such levels that it would unduly adversely affect the catalyst or its process performance, thereby requiring a separate removal step.

Illustrative examples of such dispersed liquids include aldehydes containing from 3 to 20 and more preferably 3 to 8 carbon atoms, alcohols containing from 3 to 20 and more preferably 3 to 8 carbon atoms, water, and the like. Of course, mixtures of one or more such liquids may be employed if desired. Preferably such liquids include the product aldehyde of the particular hydroformylation process involved and the corresponding alcohols of the product aldehyde, with the product aldehydes being the most preferred dispersed liquids. For example, in the case of the production of propionaldehyde, butyraldehyde and valeraldehyde, the more preferred dispersed ligand would be propionaldehyde, butyraldehyde and valeraldehyde respectively. Of course, it is to be understood that since such hydroformylation processes of $C_3$ and higher olefins produce mixtures of aldehydes e.g. propylene being hydroformylated to mixtures of n-butyraldehyde and isobutyraldehyde, the product aldehyde when employed as the dispersent liquid will also be in general, mixture of aldehydes, although individual aldehydes of such types of product aldehydes could be employed if desired. The same is true of corresponding alcohols of such product aldehydes when employed as the dispersent liquid. In general, it is preferred to employ the finally obtained purified aldehyde product of the hydroformylation process as the dispersent liquid, since such serves as an easily accessible and ready supply of dispersent liquid that should have no adverse affect whatsoever on the hydroformylation process.

The dispersing of the liquid to obtain the dispersed liquid employed in this invention that is to be contacted with the vaporized aldehyde product stream can be accomplished by a variety of devices that produce liquid droplets, since the liquid droplet size is not critical to the invention. Examples of such devices include any spray nozzles, fog nozzles, splash plates, orifices, or any similar device. This device may be in the form of many designs, its function being to provide contacting or mixing of the dispersed liquid and vaporized aldehyde product stream after it has been disengaged from the liquid catalyst containing aldehyde product solution. In general, it is preferred to employ a spray nozzle enclosed in a pipeline or vessel which will create a shower of droplets through which the aldehyde product stream is allowed to flow thereby providing a thorough contacting or mixing of the dispersed liquid and aldehyde product vapor stream. Moreover, while the dispersion of the dispersed liquid can be co-current, counter-current or cross-current with the incoming flow of the aldehyde product vapor stream, it is preferred to employ a spray nozzle in the pipeline that carries the volatilized aldehyde product stream from the separator in which said stream is disengaged from the liquid catalyst containing aldehyde product solution, that is positioned in such a fashion that the dispersed liquid droplets are counter-current to the incoming vapor flow. Of course, it is understood that more than one such spray nozzle can be employed if desired. Moreover, while the particular design of the spray nozzle employed is not critical, it of course is preferably one in which the amount of dispersed liquid contacted with the vaporized aldehyde product stream can be easily controlled. In addition, the liquid temperature of the dispersed liquid droplets to be contacted with the vaporized aldehyde product stream is not critical. The dispersed liquid temperature affects the phosphorus ligand and higher boiling aldehyde condensation by-products recovery only slightly, since the major effect in lowering the vapor temperature by contact with the dispersed liquid is from the cooling effect provided by vaporizing all or part of the dispersed liquid. Accordingly, dispersed liquid temperatures of from about 20° C. to about 80° C. should be sufficient for most purposes.

The condensed phosphorus ligand and condensed higher boiling aldehyde condensation by-products that are obtained in the form of droplets may then be separated and recovered from the remaining vaporized product stream by any suitable gas-liquid separator preferably one wherein the fluid (liquid) velocity is lowered, such that the vapor-liquid disengagement takes place by gravity force, such as vane inpingement separator. In addition, to such an initial disengagement device, it is preferred to take full advantage of the recovery system by also employing an entrainment device in the separator in addition to the initial gravity flow disengagement device to increase the overall recovery system efficiency. For instance, the aldehyde product vaporization process can also result in some inherent amount of catalyst solution entrainment and the process of contacting the dispersed liquid with the vaporized aldehyde product stream of this invention may cause any entrained drops in the vapor product stream to agglomerate into larger drops. Accordingly, such an entrainment device is essentially an extension of the initial disengagement device to increase the vapor-liquid separation efficiency and in general it is preferred to employ a mist eliminator candle filter entrainment separator. Its function is to collect any remaining liquid droplets in the vapor stream. Of course any other conventional entrainment separation device or combinations thereof may also be employed in this invention if desired e.g. which use the common variety of mechanisms including gravity, inertial impaction, interception, centrifugal force, Brownian motion and the like.

The vaporized aldehyde product so disengaged from the condensed liquid phosphorus ligand and condensed liquid higher boiling aldehyde condensation by-products can then be passed overhead and recovered in any conventional manner. If desired, said recovered aldehyde product may be even further purified by any conventional manner such as condensation and redistillation. It is important to note, however, that any further purification of the desired aldehyde product should now be more efficient and effective as a result of the subject improvement procedure of this invention.

The condensed liquid phosphorus ligand and condensed liquid higher boiling aldehyde condensation by-products collected at the bottom of the separator employed can then be recovered in any obvious fashion desired. In general, it is preferred to recycle such condensed liquid phosphorus ligand and condensed liquid higher boiling aldehyde condensation by-products directly back to the separator employed in disengaging the volatilized aldehyde products from the non-volatilized liquid catalyst containing product solution which is to be recycled back to the reactor system so as to minimize the loss of the valuable phosphorus ligand employed in the hydroformylation process.

The subject invention has uniquely discovered that by controlling the amount of dispersed liquid employed, the percentage of phosphorus ligand condensed and separated from the volatilized aldehyde product stream can be selectively promoted, while at the same time minimizing the percentage of higher boiling aldehyde condensation by-products so condensed and separated. Moreover, the ratio of phosphorus ligand recovery relative to the recovery of higher boiling aldehyde condensation by-products is dependent upon the relative volatility, i.e., the ratio of the vapor pressures of the higher boiling aldehyde condensation by-products to phosphorus ligand involved (which may be obtained by dividing the vapor pressure of such aldehyde condensation by-products by the vapor pressure of the phosphorus ligand) and the relative concentrations of each in the volatilized aldehyde product stream. The relative volatility of higher boiling aldehyde condensation by-products to phosphorus ligand of this invention may range from about 10 to about 5,000.

For instance as seen by the computerized examples herein the higher the relative volatility of the higher boiling aldehyde condensation by-products to phosphorus ligand involved, the higher the ratio of percent recovery of phosphorus ligand to percent recovery of higher boiling aldehyde condensation by-products. In addition the lower the amount of dispersed liquid employed per given flow rate of volatilized aldehyde product stream (e.g., lbs. of dispersed liquid per 1000 lbs. of the aldehyde product vapor stream) the higher the ratio of percent recovery of phosphorus ligand to percent recovery of higher boiling aldehyde condensation by-products.

Accordingly, control over the amount of dispersed liquid contacted with the vaporized aldehyde product stream provides one with wide processing latitude in obtaining wide percent recovery ratios of phosphorus ligand to higher boiling aldehyde condensation by-products and such allows one to tailor the subject invention to fit any desired given situation. For example in a hydroformylation process wherein the amount of free phosphorus ligand present in the system is small, e.g., less than 70 moles of ligand per mole of rhodium and wherein it is desirable to maintain a low concentration of higher boiling aldehyde condensation by-products, e.g., from about 0.25 to 2 percent by weight in the reaction product solution, the subject invention provides for minimizing the loss of such ligand during volalilization and separation of the aldehyde product from the reaction product solution by selectively recovering and recycling back to the system, a high percentage of the phosphorus ligand that may be contained in the vaporized aldehyde product stream, while at the same time minimizing the percentage of higher boiling aldehyde condensation by-product that may be contained in the vaporized aldehyde product stream which is also recovered and recycled with the liquid phosphorus ligand so recovered and recycled, thus also helping to prevent any undersirable build-up of the higher boiling aldehyde condensation by-products in the system.

Thus surprisingly lower amounts of dispersed liquid will be required to achieve higher ratios of percent recovery of phosphorus ligand to percent recovery of higher boiling aldehyde condensation by-products when the relative volatility of the higher boiling aldehyde condensation by-products to phosphorus ligand is low.

In general it is preferred to employ that amount of dispersed liquid which is sufficient to cause the percentage of phosphorus ligand so separated from the volatilized aldehyde product stream by the improved process of this invention to be at least 1.2 and more preferably at least 1.5 times higher than the percentage of higher boiling aldehyde condensation by-products also so separated. Of course it is to be understood that while the benefits achieved in actual practice will in general not be as high as those obtained by the computerized examples herein and while the selection of the optimum parameters and variables involved in order to obtain the best results desired will be dependent upon one's experience in the utilization of this subject improved process, only a certain minimum measure of experimentation should be necessary in order to achieve the optimum results desired for a given situation. For example in general it is considered preferable to employ only about 5 to about 60 and more preferably from about 10 to about 40 pounds per hour of dispersed liquid per a flow rate of about 1000 pounds per hour of vaporized aldehyde product stream, since such in most instances should provide an acceptable high ratio of percent recovery of phosphorus ligand to the percent recovery of higher boiling aldehyde condensation by-products.

Moreover it is to be further understood that if desire the improvement process of this invention involving contacting the volatilized aldehyde product steam with a dispersed liquid to selectively separate and recover the phosphorus ligand contained therein as compared to the concurrent separation and recovery of higher boiling aldehyde condensation by-products could, if desired, also be carried out on the gaseous aldehyde product stream as it leaves the reactor in a gas recycle hydroformylation process in order to achieve similar beneficial results.

The following examples are illustrative of the present invention and are not to be regarded as limitative. It is to be understood that all parts, percentages and proportions referred to herein and in the appended claims are by weight unless otherwise indicated.

EXAMPLES 1-6

A series of computerized (calculated) studies were conducted involving various vapor streams containing 97.7 wt. % propionaldehyde, 0.5 wt. % higher boiling aldehyde condensation by-products and different amounts (ppm) of various phosphorus ligands, the remainder consisting of lites, e.g., unreacted olefin, alkane, hydrogen and carbon-monoxide, said streams being contacted at their dew points with dispersed liquid propionaldehyde (40° C.) from a spray nozzle at a variable per hour amount rate of liquid propionaldehyde per flow rate of 1000 pounds per hour of the vaporized aldehyde product stream. The calculated relative volatility of higher boiling aldehyde by-products to phosphorus ligand involved as well as the calculated weight percent of the phosphorus ligand contained in said vapor stream as compared to the calculated weight percent of higher boiling aldehyde condensation by-products contained in said stream that may be separated and recovered from the volatilized aldehyde product stream are given in Table 1 below.

TABLE 1

| Ex. No. | Ligand | Amt. of Liquid Used[1] | Vapor Stream Dewpoint °C. | Relative Volatility[2] | Wt. % Ligand Separated | Wt. % Aldehyde Condensation By-Product Separated |
|---|---|---|---|---|---|---|
| 1 | PDPP* | 15 lbs. | 117 | 148 | 55 | 2 |
| 2 | PDPP* | 50 lbs. | 117 | 148 | 98 | 45 |
| 3 | CHDPP** | 10 lbs. | 115 | 260 | 49 | 1 |
| 4 | CHDPP** | 40 lbs. | 115 | 260 | 98 | 40 |
| 5 | TPP*** | 10 lbs. | 133 | 1730 | 44 | 0.1 |
| 6 | TPP*** | 50 lbs. | 133 | 1730 | 96 | 0.5 |

[1]Pounds of liquid employed per flow rate of 1000 lbs. of vaporized aldehyde product stream.
[2]Relative Volatility of Aldehyde Condensation By-Products to Ligand Employed
*PDPP = propyldiphenylphosphine (100 ppm).
**CHDPP = cyclohexyldiphenylphosphine (50 ppm).
***TPP = triphenylphosphine (30 ppm).

EXAMPLES 7-10

A series of computerized (calculated) studies were conducted involving various vapor streams containing 87.6 wt. % butyraldehyde. 0.3 wt. % higher boiling aldehyde condensation by-products and different amounts (ppm) of various phosphorus ligands, the remainder consisting of lites e.g., unreacted olefin, alkane, hydrogen and carbon monoxide, said streams being contacted at their dew points with dispersed liquid butyraldehyde (40° C.) from a spray nozzle at a variable per hour amount rate of liquid butyraldehyde per flow rate of 1000 pounds per hour of the vaporized aldehyde product stream. The calculated relative volatility of higher boiling aldehyde by-products to phosphorus ligand involved as well as the calculated weight percent of the phosphorus ligand contained in said stream as compared to the calculated weight percent of higher boiling aldehyde condensation by-products contained in said vapor stream that may be separated and recovered from the volalitized aldehyde product stream are given in Table 2 below.

TABLE 2

| Ex. No. | Ligand | Amt. of Liquid Used[1] | Vapor Stream Dewpoint °C. | Relative Volatility[2] | Wt. % Ligand Separated | Wt. % Aldehyde Condensation By-Product Separated |
|---|---|---|---|---|---|---|
| 7 | PDPP* | 10 lbs. | 146 | 224 | 32 | 0.2 |
| 8 | PDPP* | 60 lbs. | 146 | 224 | 93 | 2 |
| 9 | TPP** | 10 lbs. | 138 | 375 | 38 | 0.2 |
| 10 | TPP** | 60 lbs. | 138 | 375 | 99 | 3 |

[1] Pounds of liquid employed per flow rate of 1000 lbs. of vaporized aldehyde product stream.
[2] Relative Volatility of Aldehyde Condensation By-Products to Ligand Employed
*PDPP = propyldiphenylphosphine (125 ppm).
**TPP = triphenylphosphine (50 ppm).

EXAMPLES 11–16

A series of computerized (calculated) studies were conducted involving various vapor streams containing 91.8 wt. % valeraldehyde, 0.5 wt. % higher boiling aldehyde condensation by-products and different amounts (ppm) of various phosphorus ligands, the remainder consisting of lites, e.g., unreacted olefin, alkane, hydrogen and carbon monoxide, said streams being contacted at their dew points with dispersed liquid valeraldehyde (40° C.) from a spray nozzle at a variable per hour amount rate of liquid valeraldehyde per flow rate of 1000 pounds per hour of the vaporized aldehyde product stream. The calculated relative volatility of higher boiling aldehyde by-products to phosphorus ligand involved as well as the calculated weight percent of the phosphorus ligand contained in said vapor stream as compared to the calculated weight percent of higher boiling aldehyde condensation by-products contained in said stream that may be separated and recovered from the volalitized aldehyde product stream are given in Table 3 below.

EXAMPLE 17

A continuous liquid recycle hydroformylation process wherein butene-1 was hydroformylated into $C_5$ aldehyde with carbon monoxide and hydrogen in the presence of a rhodium-phosphorus complex catalyst, free cyclohexyldiphenylphosphine ligand and higher boiling $C_5$ aldehyde condensation by-products was operated over a three-day period. The liquid catalyst containing $C_5$ aldehyde product reaction solution after removal from the hydroformylation reactor was vaporized to obtain a vaporized $C_5$ aldehyde product stream, estimated to contain a 91.8 weight percent $C_5$ aldehyde mixture of valeraldehyde and 2-methylbutyraldehyde, 0.35 weight percent higher boiling $C_5$ aldehyde condensation by-products and 100 ppm cyclohexyldiphenylphosphine ligand, which was disengaged in a separator from the remaining non-volatilized liquid catalyst containing reaction solution, said reaction solution being recycled back to the hydroformylation reactor. The relative volatility of the higher boiling $C_5$ aldehyde condensation by-products to the cyclohexyldiphenylphosphine ligand in said solution was about 18. Said vaporized $C_5$ aldehyde product stream was passed into a pipe into which some of the resultant purified (condensed and reflux) liquid $C_5$ aldehyde product at 40° C. of the involved hydroformylation process was sprayed through a spray nozzle in a counter-current fashion to the flow of the vaporized $C_5$ aldehyde product stream and at a rate of about 26 pounds per hour of liquid $C_5$ aldehyde product per flow rate of about 1000 pounds per hour of the vaporized aldehyde product stream.

The liquid droplets of $C_5$ aldehyde product vaporized to cool the $C_5$ aldehyde product vapor stream below its dewpoint and form droplets of cyclohexyldiphenylphosphine ligand and higher boiling $C_5$ aldehyde condensation by-products. The vapor containing said condensed droplets was fed to a gas-liquid separator wherein the vapor was first passed through a vane impingement separator and then a mist eliminator candle

TABLE 3

| Ex. No. | Ligand | Amt. of Liquid Used[1] | Vapor Stream Dewpoint °C. | Relative Volatility[2] | Wt. % Ligand Separated | Wt. % Aldehyde Condensation By-Product Separated |
|---|---|---|---|---|---|---|
| 11 | PDPP* | 10 lbs. | 145 | 15 | 47 | 14 |
| 12 | PDPP* | 50 lbs. | 145 | 15 | 91 | 68 |
| 13 | CHDPP** | 10 lbs. | 144 | 18 | 53 | 16 |
| 14 | CHDPP** | 40 lbs. | 144 | 18 | 90 | 60 |
| 15 | TPP*** | 10 lbs. | 149 | 80 | 53 | 3 |
| 16 | TPP*** | 50 lbs. | 149 | 80 | 98 | 52 |

[1] Pounds of liquid employed per flow rate of 1000 lbs. of vaporized aldehyde product stream.
[2] Relative Volatility of Aldehyde Condensation By-Products to Ligand Employed
*PDPP = propyldiphenylphosphine (150 ppm).
**CHDPP = cyclohexyldiphenylphosphine (100 ppm).
***TPP = triphenylphosphine (80 ppm).

filter entrainment separator in order to disengage the vaporized $C_5$ aldehyde product stream from said condensed liquid, which droplets were collected from the bottom of said gas-liquid separator and recycled through a line to the initial separator wherein the vaporized $C_5$ aldehyde product was disengaged from the non-volatilized liquid catalyst containing reaction product solution. The disengaged $C_5$ aldehyde product stream leaving said gas-liquid separator was then condensed into liquid to recover crude $C_5$ aldehyde product. Analysis of various samples of crude $C_5$ aldehyde product showed it to contain about 26 ppm (wt. %) cyclohexyldiphenylphosphine and about 0.23 to 0.33 wt. % higher boiling $C_5$ aldehyde condensation by-products. Such analysis indicates that an estimated 74 percent of the cyclohexyldiphenylphosphine ligand and about 6 to 34 percent of the higher boiling $C_5$ aldehyde condensation by-products contained in the vaporized $C_5$ aldehyde product stream disengaged from the liquid catalyst containing product reaction solution had been separated and removed from said vaporized $C_5$ aldehyde product stream.

When carrying out the hydroformylation process with the liquid spray of $C_5$ aldehyde product turned off the crude aldehyde product liquid was observed to have contained about 100 ppm of cyclohexyldiphenylphosphine and about 0.35 weight percent of higher boiling $C_5$ aldehyde condensation by-products.

Various modifications and variations of this invention will be obvious to a worker skilled in the art and it is to be understood that such modifications and variations are to be included within the purview of this application and the spirit and scope of the appended claims.

We claim:

1. In a liquid recycle rhodium catalyzed hydroformylation process for producing aldehydes, wherein an olefinic compound, carbon monoxide and hydrogen are reacted in the presence of a solubilized rhodium-phosphorus complex catalyst, free phosphorus ligand and higher boiling aldehyde condensation by-products to produce an aldehyde product and wherein said aldehyde is separated and recovered from a liquid reaction aldehyde product solution containing aldehyde product, solubilized rhodium-phosphorus complex catalyst, free phosphorus ligand and higher boiling aldehyde condensation by-products that has been removed from the hydroformylation reactor, by vaporizing the aldehyde product contained in said solution to obtain a vaporized aldehyde product stream consisting essentially of aldehyde product, vaporized phosphorus ligand and vaporized higher boiling aldehyde condensation by-products which is disengaged in a separator from the remaining non-volatilized catalyst containing liquid reaction product solution that is recovered from the bottom of the separator and recycled back to the reaction system, the improvement which comprises (a) selectively separating the phosphorus ligand contained in said vaporized aldehyde product stream by thoroughly contacting said stream with a spray of dispersed liquid having a lower boiling point than said higher boiling aldehyde condensation by-products so as to condense the vaporized phosphorus ligand and vaporized higher boiling aldehyde condensation by-products contained in said volatilized aldehyde product stream, and (b) recovering the condensed phosphorus ligand and condensed higher boiling aldehyde condensation by-products so obtained from said volatilized aldehyde product stream, said dispersed liquid being employed in the form of droplets and in an amount such that the percent of phosphorus ligand so separated and recovered is at least 1.2 times higher than the percent of higher boiling aldehyde condensation by-products also so separated and recovered and wherein the amount ratio of dispersed liquid employed per flow rate of volatilized aldehyde product stream is about 5 to 60 pounds per hour of dispersed liquid per 1000 pounds per hour of volatilized aldehyde product stream.

2. A process as defined in claim 1, wherein the olefinic compound is an olefin having from 2 to 8 carbon atoms.

3. A process as defined in claim 2, wherein the amount ratio of dispersed liquid employed per flow rate of volatilized aldehyde product stream is about 10 to 40 pounds per hour of dispersed liquid per 1000 pounds per hour of volatilized aldehyde product stream.

4. A process as defined in claim 2, wherein the phosphorus ligand is a triorganophosphine compound.

5. A process as defined in claim 3, wherein the ligand is triphenylphosphine.

6. A process as defined in claim 3, wherein the ligand is cyclohexyldiphenylphosphine.

7. A process as defined in claim 2, wherein the relative volatility of the higher boiling aldehyde condensation by-products to phosphorus ligand is from about 10 to about 5000.

8. A process as defined in claim 2, wherein the recovered condensed phosphorus ligand and condensed higher boiling aldehyde condensation by-products so separated from the vaporized aldehyde product stream are recycled to the separator in which said vaporized aldehyde product stream was disengaged from the non-volatilized liquid catalyst containing reaction product solution.

9. A process as defined in claim 1, wherein the dispersed liquid is selected from the group consisting of aldehydes containing from 3 to 20 carbon atoms, alcohols containing from 3 to 20 carbon atoms, water and mixtures thereof.

10. A process as defined in claim 9, wherein the dispersed liquid is an aldehyde containing from 3 to 8 carbon atoms or a mixture of such aldehydes.

11. A process as defined in claim 9, wherein the dispersed liquid is a mixture of aldehydes or an individual aldehyde corresponding to the product aldehyde of the particular hydroformylation process involved.

12. A process as defined in claim 3, wherein the dispersed liquid is an aldehyde containing from 3 to 8 carbon atoms or a mixture of such aldehydes.

13. A process as defined in claim 12 wherein the dispersed liquid is a mixture of aldehydes or an individual aldehyde corresponding to the product aldehyde of the particular hydroformylation process involved.

* * * * *